US006607274B2

United States Patent
Stantz et al.

(10) Patent No.: US 6,607,274 B2
(45) Date of Patent: Aug. 19, 2003

(54) METHOD FOR COMPUTING VISUAL PERFORMANCE FROM OBJECTIVE OCULAR ABERRATION MEASUREMENTS

(75) Inventors: Keith Stantz, Indianapolis, IN (US); Daniel R. Neal, Tijeras, NM (US); Ron Rammage, Tijeras, NM (US)

(73) Assignee: WaveFront Sciences, Inc., Albuquerque, NM (US)

( * ) Notice: Subject to any disclaimer, the term of this patent is extended or adjusted under 35 U.S.C. 154(b) by 0 days.

(21) Appl. No.: 10/115,037

(22) Filed: Apr. 4, 2002

(65) Prior Publication Data

US 2002/0186346 A1 Dec. 12, 2002

Related U.S. Application Data

(63) Continuation of application No. PCT/US01/32505, filed on Oct. 19, 2001.
(60) Provisional application No. 60/241,789, filed on Oct. 20, 2000.

(51) Int. Cl.[7] .................................................. A61B 3/10
(52) U.S. Cl. ....................................................... 351/221
(58) Field of Search ................................. 351/205, 206, 351/211, 212, 214, 221, 237, 239, 241, 242, 243; 348/607

(56) References Cited

U.S. PATENT DOCUMENTS 5,272,533 A * 12/1993 Akiyama et al. ........... 348/607

OTHER PUBLICATIONS

Junzhong Liang, "Objective measurement of wave aberrations of the human eye with the use of a Hartmann–Shack wave–front sensor," 1994 Optical Society of America, vol. 11, No. 7, Jul. 1994, J. Pt. Soc. Am. A, pp. 1949–1957.
John e. Greivenkamp et al., "Visual Acuity Modeling Using Optical Raytracing os Schematic Eyes," American Journal of Ophthalmology 1995, pp. 227–240.

Donald T. Miller, "Retinal Imaging and Vision at the Frontiers of Adaptive Optics," Jan. 2000 Physics Today, pp. 31–36.

J. Primot et al., "Deconvolution from wave–front sensing: a new technique for compensating turbulence–degrated images," 1990 Optical Society of America, Sep. 1990, No. 9, pp. 1598–1608.

Junzhong Liang et al., "Supernormal vison and high–resolution retinal imaging through adaptive optics," J. Opt.Soc. Am. A/vol. 14, No. 11, Nov. 1997, pp. 2884–2892.

Brian A. Barsky et al., "Corporating Camera Models, Ocular Models, and Actual Patient Eye Data for Photo–Realistic and Vision–Realistic Rendering," pp. 1–10.

Ester Moreno–Barriuso et al., "Laser Ray Tracing versus Hartmann–Shack sensor for measuring optical aberrations in the human eye," J. Opt. soc. Am. A, vol. 17, No. 6, Jun. 2000, pp. 974–985.

Daniel Dante Garcia, "CWhatUC:Software Tools for Predicting, Visualizing and Simulating Corneal Visual Acuity," University of California at Berkeley, dissertation, pp. 1–196.

* cited by examiner

Primary Examiner—George Manuel

(57) ABSTRACT

A method for computing the visual performance of a human or animal subject based on objective measurements of visual refraction, including higher order aberrations, includes measuring wavefront aberrations of a subject ocular pupil, computing a point-spread-function from the measured pupil aberration, providing a test image, and convolving the test image with the point-spread-function. A simulated image may be produced from the convolution result of the test image with the point-spread-function. One or more specific terms of the point-spread-function may be subtracted therefrom prior to the convolving step to simulate an effect of a correcting means, such as spectacles lenses, contact lenses, or laser surgery. A best correction for a given subject may be determined by adjusting the terms that are subtracted to optimize the resultant image.

21 Claims, 4 Drawing Sheets

Target    Fully Resolved    Just Resolved    Unresolved
                            (Rayleigh)

METHOD FOR COMPUTING VISUAL PERFORMANCE FROM OBJECTIVE OCULAR ABERRATION MEASUREMENTS

CROSS REFERENCE TO RELATED APPLICATIONS

This is a continuation application claiming the priority benefit under 35 U.S.C. §119 of International Application Serial No. PCT/US01/32505 filed on Oct. 19, 2001, under 35 U.S.C. §119, and U.S. Provisional Patent Application No. 60/241,789 filed on Oct. 20, 2000, the entirety of each of which is hereby incorporated by reference for all purposes as if fully set forth herein.

BACKGROUND OF THE INVENTION

1) Field of the Invention

This invention pertains to the field of characterization and measurement of human and animal visual performance, and more particularly, to a method of performing objective measurement of human and animal visual performance.

2) Description of the Related Art

Traditional measures of human and animal visual performance have been limited by the need for subjective feedback from patients, or to examination of a limited number of parameters. The Snellen chart is often used to measure the visual acuity of the subject. The visual acuity is defined in terms of the ability to distinguish letters or shapes in a standard chart, the size of the letters that can be recognized being a measure of the optical system performance of the eye.

Unfortunately, the most common method for measuring visual performance, subjective refraction, cannot be applied to animal subjects used for research, for very young children, or those with learning or communication difficulties. New instruments have been developed in recent years to make objective measurements of the eye. These instruments include: autorefractors for measuring the basic refractive error; corneal topography instruments that can measure the corneal surface; and a variety of aberrometers that have recently been shown to be able to measure higher order aberrations. With each new advance, more information can be measured about the eye.

Auto-Refractor.

The auto-refractor is an instrument that uses one of a variety of methods to analyze the cornea and lens of an eye to determine the basic refractive error. This error is presented in terms of the spherical and cylindrical power of a lens that is needed for its correction. In the event that higher order irregularities are present, these are included only in the effect that they have on the overall visual performance.

Corneal Topography.

A corneal topography instrument uses one of a number of techniques to measure the shape of the cornea. Since this shape is, in many cases, the source of the aberrations, it provides a useful and more complete measure of the optical performance of the eye. The information can be used to predict the visual acuity and optical performance with greater accuracy than using the sphero-cylinder terms alone. However, assumptions about the interior structure of the eye must be made in inferring the visual performance from corneal topography measurements alone.

Aberrometer (Also Known as Wavefront Analyzer).

The aberrometer is a system for measuring the aberrations of the eye by projecting light onto the retina and thus observing the effect of the entire ocular optical system. Using these methods both the basic refractive error (spherocylinder) and higher order aberrations may be determined. However, since this represents a measurement of the full optical path through the eye, a complete estimate of all the important optical effects can be obtained. It is not necessary to make assumptions about the internal or external structure of the eye since the aberrations can be measured directly. An objective aberrometer does not rely on subjective feedback, but measures the aberrations by projecting light into the eye and measuring it using objective means.

Given this new level of accurate information that can be determined about the eye, it remains an important task for the clinician to interpret the data in light of both the historical measures, and in terms that can be readily understood by patients. For example, Mrochen, Kaemmerer, Mierdel and Seiler used an objective aberrometer to measure the effect of laser refractive surgery on ocular aberrations. Mrochen, Kaemmerer, Mierdel and Seiler, 27 J. CATARACT REFRACT SURG. (March 2001). But while they were able to relate their results in terms of the optical aberrations of the eye, they were not able to make the connection to patient satisfaction or degradation in visual acuity in scotopic conditions. While the aberrometer is capable of providing a precise wavefront map of the aberrations of the optical system, unless the information can be interpreted by the clinician or researcher, it may have little value for diagnosis and treatment.

There are a number of methods currently used to measure performance of the ocular system. The most widely used and well established are psycho-physical methods, i.e., methods relying on subjective patient feedback. The oldest of the psycho-physical methods is the phoropter or trial lens method, which relies on trial and error to determine the required correction. There are psycho-physical methods for measuring visual acuity, ocular modulation transfer function, contrast sensitivity and other parameters of interest. While new advances in this field continue (see, e.g., PCT Publication No. WO 93/002614, European Patent Number 00600963/EP B1), they rely on subjective feedback and hence suffer from the limitations cited above.

In addition to these subjective methods, there are also objective methods for assessing the performance of the ocular system. Such objective methods include corneal topography, wavefront aberrometry, corneal interferometry, and auto-refraction. Many of these methods only measure the contribution of specific elements to the total refractive error. For example, much work has been directed to measuring the topography of the cornea and characterizing the corneal layer. However, the corneal shape only contributes about 30–40% of the total refractive error in most cases. In order to measure the bulk of the refractive error and to provide a complete mapping for diagnosis and correction, additional information and measurements are needed.

Another method for determining the refraction of the eye is auto-refraction, which uses a variety of techniques to automatically determine the required corrective prescription. These automated techniques include projecting one or more spots or patterns onto the retina, automatically adjusting optical elements in the auto-refractor until the desired response is achieved, and determining the required correction from this adjustment. However, auto-refractors are not considered especially reliable. Further, auto-refractors measure only lower order components of the aberrations, e.g., focus and astigmatic errors.

Recently, the eye has been considered an optical system, leading to the application of methods previously used for other optical systems to the measurement of the eye. These methods include interferometry and Shack-Hartmann wavefront sensing. These techniques are of particular interest because they measure the complete aberrations of the eye. These include the low order aberrations such as defocus and astigmatism, as well as higher order aberrations such as coma, spherical aberration or other more rapidly varying components. This additional information allows measurement of non-uniform, asymmetric errors that may be affecting vision. Further, this information may be linked with any of the various corrective techniques to provide improved vision. For example, U.S. Pat. No. 5,777,719 to Williams describes the application of Shack-Hartmann wavefront sensing and adaptive optics for correcting ocular aberrations to make a super-resolution retina-scope. U.S. Pat. No. 5,949,521 to Williams et al. describes using this information to make better contacts, intra-ocular lenses and other optical elements. Several types of objective aberrometers have been developed which can provide the wavefront information. These include the Shack-Hartmann (or Hartmann-Shack), Moiré deflectometry, Tscheming aberrometer, scanning resolved refractometer (ray-tracing), and a variety of other wavefront aberrometer technologies.

Wavefront aberrometry measures the full, end-to-end aberrations through the entire optics of the eye. In these measurements, a spot is projected onto the retina, and the resulting returned light is measured with an optical system, thus obtaining a full, integrated, line-of-sight measurement of the eye's aberrations. U.S. patent application Ser. No. 09/692,483 describes a method for designing practical clinical instruments for measuring full, end-to-end aberrations through the entire optics of the eye.

Williams, and others, have been able to use a full adaptive optics system to present a corrected eye chart to a subject. However, this is still not useful for determining the objective visual acuity. While such a system can produce images with arbitrary effects included (up to the mechanical ability of the deformable mirror components), it introduces a significant additional cost and complexity.

Camp, McGuire, Cameron and Robb attempted to simulate the image quality and visual performance based on a model of the internal structure and measurements of the corneal surface. 109 AM. J. OPHTHALMOLOGY 4 (Apr. 15, 1990). Klonos, Pallikaris and Fitzke extended this work using an improved model of the internal structure. 12 J. REFRACT. SURG. 2 (February 1996). Barsky, Garcia, Klein, and Van De Pol reported a method for computing the visual acuity from the wavefront inferred from corneal topography measurements and a model of the interior structure of the eye in SPIE 3591, pp. 303–310 (1999). In these cases the internal structure of the eye was simulated based on a priori assumptions.

While ray-tracing and other techniques have attempted to predict visual acuity based on the refraction or corneal topography data, in all cases these relied on assumptions, rather than measurements, of the ocular optical system.

Accordingly, it would be advantageous to provide a method is needed to predict visual acuity and other ocular performance metrics from the aberrometry data. In particular, it would be advantageous to provide a method of evaluating of visual performance that relies on only measured values for the ocular aberrations. It would also be advantageous to provide a method for computing the ocular performance, predicting the appearance of images viewed by a subject, and determining the visual acuity in an objective fashion. Other and further objects and advantages will appear hereinafter.

SUMMARY OF THE INVENTION

The present invention comprises a method for computing the visual performance of a human or animal subject by using measurements of the subject's aberrations obtained from an aberrometer that measures the full aberrations through the ocular optical system.

In one aspect of the invention, a method for computing the visual performance of a human or animal subject based on objective measurements of visual refraction including higher order aberrations, includes measuring wavefront aberrations of a subject ocular pupil, computing a point-spread-function from the measured pupil aberration, providing a test image, and convolving the test image with the point-spread-function. Beneficially, a simulated image, that is similar to a subject's view, is produced from the convolution result of the test image with the point-spread-function. Also beneficially, the convolution of the test image with the point-spread-function includes performing an inverse Fourier transform of a modulus squared of the point-spread-function to compute an optical transfer function, computing a Fourier transform of the test image, and computing an inverse Fourier transform of a product of the optical transfer function and the test image Fourier transform.

Moreover, in another aspect of the invention, the subject's visual acuity and visual acuity number can be determined objectively from these computations. In that case, the test image may be a Snellen acuity chart.

In another aspect of the invention, a method for computing an image, includes measuring wavefront aberrations of a subject ocular pupil, computing a point-spread-function from the measured pupil aberration, providing a test image, convolving the test image with the point-spread-function, and producing a simulated image from a convolution result of convolving the test image with the point-spread-function, wherein at least one specific term of the point-spread-function is adjusted prior to the convolving step to simulate an effect of a correcting means. Beneficially, adjusting the specific term comprises subtracting or eliminating the specific term, e.g., by setting a high order Zernike coefficient in the pupil aberration function to zero.

In yet another aspect of the invention, a method for computing an effect of corrective means on a subject's visual acuity, includes measuring a subject pupil aberration function with an objective aberrometer, adjusting (e.g., adding or subtracting) terms to the measured subject pupil aberration function that correspond to specific corrective means, producing a modified pupil aberration function, computing a point-spread-function from the modified pupil aberration function, computing an optical transfer function (OTF) of the computed point-spread-function, multiplying a Fourier transform of a test image by the OTF to produce a Fourier result, and performing an inverse Fourier transform on the Fourier result. The corrective means may be spectacle lenses, contact lenses, laser refractive surgery, or Laser Thermal Keratotomy.

In still another aspect of the invention, a method of determining a best correction for a given subject, includes measuring a subject pupil aberration function with an objective aberrometer, subtracting terms from the pupil aberration function that correspond to specific corrective means, producing a modified pupil aberration function, computing a point-spread-function from the modified pupil aberration function, computing an optical transfer function (OTF) of the computed point-spread-function, multiplying a Fourier transform of a test image by the OTF to produce a Fourier result, performing an inverse Fourier transform on the Fourier result, and adjusting the terms that are subtracted to optimize a resultant image.

BRIEF DESCRIPTION OF THE DRAWINGS

FIG. 6A shows a cross section through the original target, FIG. 6B shows a resolved image of the target, FIG. 6C shows the target image that just meets the Rayleigh criterion, and FIG. 6D shows an unresolved image.

DESCRIPTION OF THE PREFERRED EMBODIMENTS

Figure 1A:
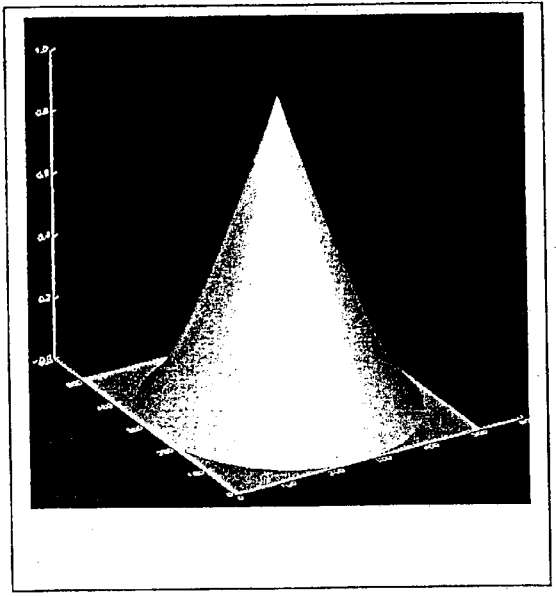
FIG. 1A shows the Modulation Transfer Function (MTF) for an eye with perfect vision.

Embodiments and other aspects of the invention described herein, including the system embodiments described below, may be made or used in conjunction with inventions described, in whole or in part, in co-pending U.S. patent application Ser. No. 09/692,483, filed on Oct. 20, 2000, filed in the name of inventors Daniel R. Neal, Darrel Armstrong, James Gruetzner, and James Copland, entitled "Dynamic Range Extension Techniques for a Wavefront Sensor Including Use in Ophthalmic Measurement," the entirety of which is hereby incorporated herein by reference for all purposes as if fully set forth herein.

This invention relies on a measurement of the aberrations, including both the low and high orders to calculate the effect of these aberrations on an image. The aberrometer generates a measured map of the appropriate aberrations, which may be expressed either in terms of a wavefront error distribution, or in terms of a set of representative polynomials. This map, which may be called the pupil aberration function, can be analyzed to predict the effect of these aberrations on the image.

The method described herein consists of two basis steps:

1. Computation of the point-spread-function. That is, the response of the measured optical system to a single point source; and
2. Convolution of the point-spread-function with an appropriate image.

These steps are the minimum necessary to evaluate the effect of the aberrations on visual acuity. The point-spread-function may be computed from the aberration map alone, with no a priori assumptions about the internal structure of the eye. Any image can be used for the second, convolution, step. This can be a scene, a color or black and white image, a letter or series of letters, a Snellen acuity chart, or a pattern of geometric shapes that may be useful for determining other properties of vision.

It may be possible to perform both operations at once by taking advantage of certain properties of the Fourier transform. Both the point-spread-function and convolution operations may be performed using Fourier-transform techniques.

Some specific shapes can be used to determine the Snellen Acuity number, or objective visual acuity. The simplest such shape is a pair of points. When convolved with the point-spread-function, the visual acuity number may be related to the resolvable separation of the points. An absolute criterion, such as the Rayleigh criterion, may be used to determine this number from the data. Better targets, such as a series of bars at different separations may be more readily interpreted automatically.

It is also possible to compute the visual acuity directly from the point-spread-function by analyzing its spatial extent. Since the point-spread-function (by definition) is the response of the optical system to a point input, the spatial extent of this function contains all the information needed to compute the visual acuity number. An appropriate algorithm can be used to objectively determine the spatial extent, such as $2^{nd}$ moment, or fitting to a Gaussian profile or other a priori shapes.

Algorithm.

A wavefront aberrometer measures the full aberrations of the eye (e.g., cornea and lens) to provide the pupil aberration function $\phi(x,y)$. Beneficially, the wavefront aberrometer is an objective aberrometer that measures the low order aberrations such as defocus and astigmatism, as well as higher order aberrations such as coma, spherical aberration or other more rapidly varying components. With this information, it is possible to simulate how these aberrations reduce the fidelity of a subject's eyesight, i.e., to visualize a patient's lack of acuity. The procedure follows these steps:

(1) construct the impulse response function, or point-spread-function (PSF), of the cornea and lens using either the fitted Zernike coefficients from measured data or a measured wavefront map;

(2) perform the inverse Fourier transform of the intensity-PSF (modulus squared of the PSF) to produce the measured optical transfer function (OTF);

(3) multiply the OTF with the spectral distribution of an image (e.g., eye chart); and (4) calculate the inverse Fourier transform to simulate how a patient's visual acuity affects his or her eyesight.

The first step is to form the generalized pupil aberration function, P, utilizing measured sensor data.

$$P(x,y) = P(x,y) \cdot e^{j\phi(x,y)}, \quad (1)$$

where $P(x,y)$ is the pupil aberration function, $$P(x,y) = P(\rho,\theta) = circ(\rho), \quad (2)$$

and the wavefront may be represented by the phase function:.

$$\phi(\rho, \theta) = k \cdot \sum_{n=1}^{15} z_n \cdot P_n(\rho, \theta), \quad (3)$$

where $z_n$ represents the coefficients for the Zernike polynomials $P_n$ (see, e.g., MALACARA, OPTICAL SHOP TESTING, p. 455–499, John Wiley & Sons 1992) and k is the wave-number of the laser source, $2\pi/k$. The pupil aberration function may be expressed as an expansion in terms of known polynomials, e.g. Zernike polynomials, or as a distribution map of wavefront values, determined numerically or analytically. From P the PSF is calculated by taking the Fourier transform $F\{\ \}$:

$$PSF=F\{P(x,y)\}. \quad (4)$$

The next step solves for the OTF to be used for incoherent illumination. It is the normalized autocorrelation function of the intensity impulse response function, the magnitude squared of the PSF.

$$OTF = \frac{F^{-1}\{PSF^* \cdot PSF\}}{\pi \cdot r^2}, \quad (5)$$

where r is the pupil radius.

Convolution takes place in the frequency domain. The OTF is multiplied by the spectral content of an image, e.g., the Fourier transform of the eye chart input image. The final step performs the inverse Fourier transform on the above product to determine the form of the image on the retina (see FIGS. 1B, 2B, 3B and 4B).

$$\text{Retinal image}=|F^{-1}\{OTF \cdot F\{\text{image}\}\}| \quad (6)$$

Computational Considerations.

Two inter-related issues include how to sample the image and the sampling resolution of the above calculation. The resolution of an image on the retina (i.e., sampling rate) is defined by the minimal distance between rods or cones, which is 1.5–2.0 $\mu$m. Therefore, an image placed one focal length in front of the eye has a magnification of 1 and the same spatial resolution. Therefore, all eye charts represent letter sizes and line-widths with a specific number of pixels. This has been measured and tabulated in Table 1 below.

TABLE 1

Resolution requirements for simulating letters in an Eye Chart

| Visual Acuity | Eye Chart | samples |
|---|---|---|
| 20/200 | E | 185.2 |
| 20/100 | F P | 92.6 |
| 20/70 | T O Z | 64.8 |
| 20/50 | L P E D | 46.3 |
| 20/40 | P E C F D | 37.0 |
| 20/30 | E D F C Z P | 27.8 |
| 20/25 | F E L O P Z D | 23.2 |
| 20/20 | D E F P O T E C | 18.5 |

The Fourier transforms may advantageously be computed using Fast Fourier Transform (FFT) techniques.

The eye chart displays the letter E for the following levels of visual acuity: 20/200, 20/100, 20/50, 20/40, 20/30, and 20/20 (FIGS. 1B, 2B, 3B and 4B). Defining the retinal sample size to 2 $\mu$m, the number of samples is 512. This sample size ignores the diffractive effects of the pupil, only the effects of the aberrations on the object are simulated.

FIGS. 1–4 display the Modulation Transfer Function and visual acuity charts. (eye chart simulations) for the following cases: perfect visual acuity ($z_n$0) (FIGS. 1A–B); vision with slight defocus ($z_5 \sim \lambda/4$) (FIGS. 2A–B); vision with a lot of defocus ($z_5 \sim 2\%$) (FIGS. 3A–B); and the vision of a human subject (FIGS. 4A–B). The Modulation Transfer Function (MTF) is the modulus of the Optical Transfer Function (OTF), which is a complex function.

Figure 1B:
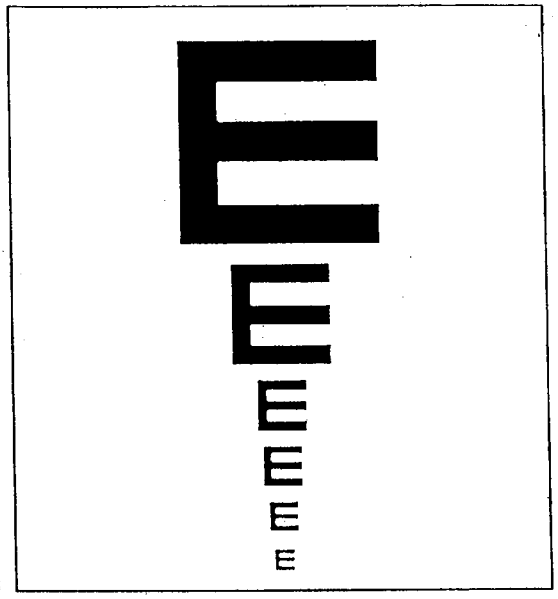
FIG. 1B shows a corresponding visual acuity chart computed according to a preferred embodiment of the invention.

FIG. 1A shows the MTF for an eye with perfect vision, i.e., excellent visual acuity, no aberrations measured (i.e., Zernike coefficients approach zero). This produces an MTF having nearly a perfect cone shape. The degradation in acuity is only a result of the fact that the image was transmitted through a finite pupil. FIG. 1B shows an eye chart simulation produced by the convolution of the OTF whose MTF is shown in FIG. 1A, with an exemplary eye chart.

Figure 2A:
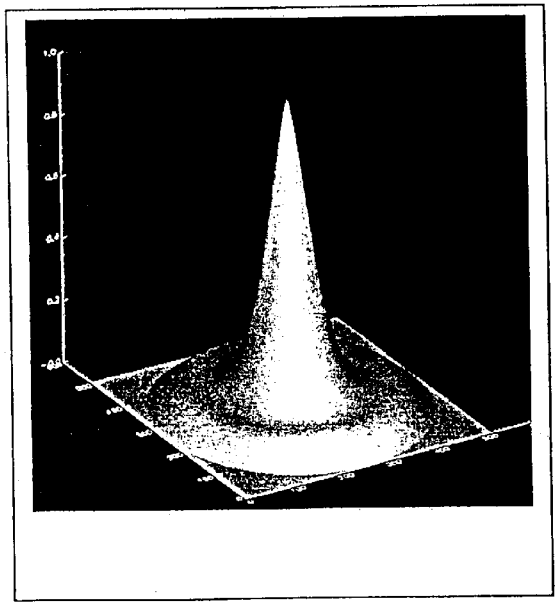
FIG. 2A shows the MTF of an eye having a weak aberration, $V_4$ wave of defocus.
Figure 2B:
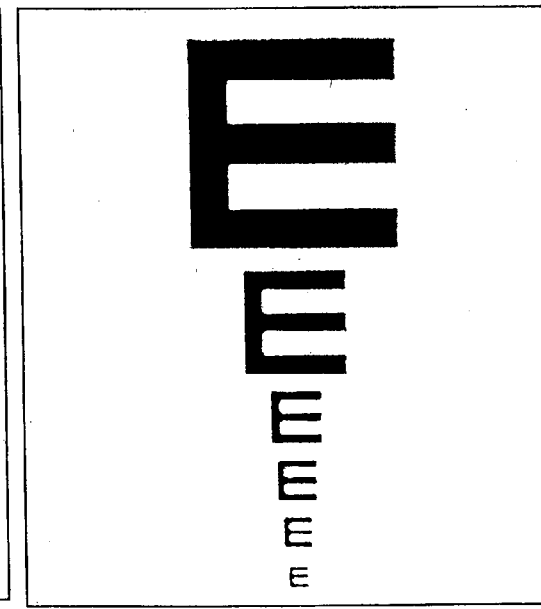
FIG. 2B shows a corresponding visual acuity chart computed according to a preferred embodiment of the invention.
Figure 3A:
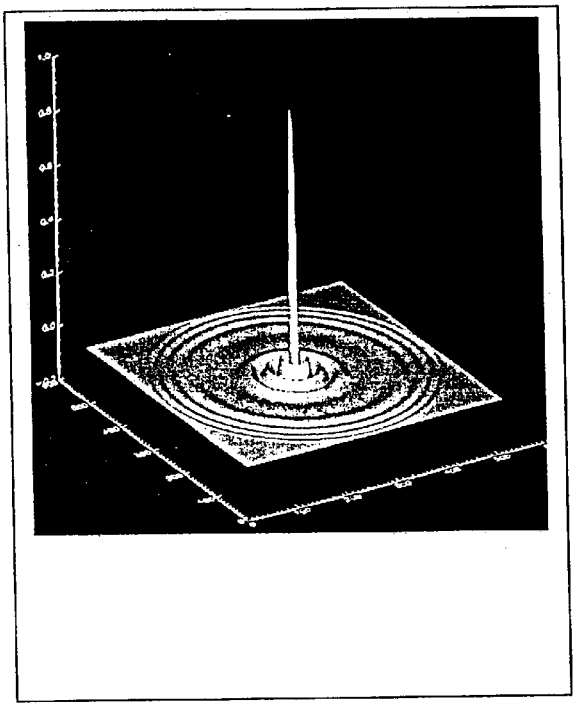
FIG. 3A shows the MTF of an eye having a significant aberration, 2 waves of defocus.
Figure 3B:
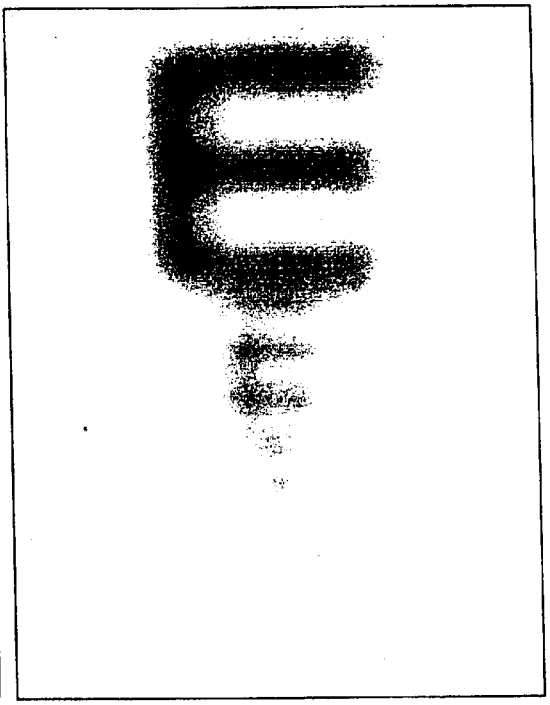
FIG. 3B shows a corresponding visual acuity chart computed according to a preferred embodiment of the invention.

Aberrations distort the OTF and thus an image. Slowly increasing the defocus term (Zernike coefficient five) attenuates higher frequency acuity causing edges to appear "fuzzy." As an example, FIG. 2A shows the MTF of an eye having a weak defocus term, ¼ wave of defocus, and FIG. 2B shows the an eye chart simulation produced by convolution of the OTF whose MTF is shown in FIG. 2A, with the exemplary eye chart of FIG. 1B. A slice of the MTF cone through the origin appears "L-shaped." As this aberration becomes worse ($>\lambda/2$), the OTF can change sign, an indication of contrast reversal. FIG. 3A shows the effect of a significant aberration, 2 waves of defocus, on the MTF, and FIG. 3B shows the corresponding acuity chart (eye chart simulation) obtained by convolution of the OTF whose MTF is shown in FIG. 3A, with the exemplary eye chart of FIG. 1B. While the aberrations are still symmetric, a significant effect is evident. Oscillations in the MTF, reversals in contrast, and the loss of visual acuity (20/100) are noted.

Figure 4A:
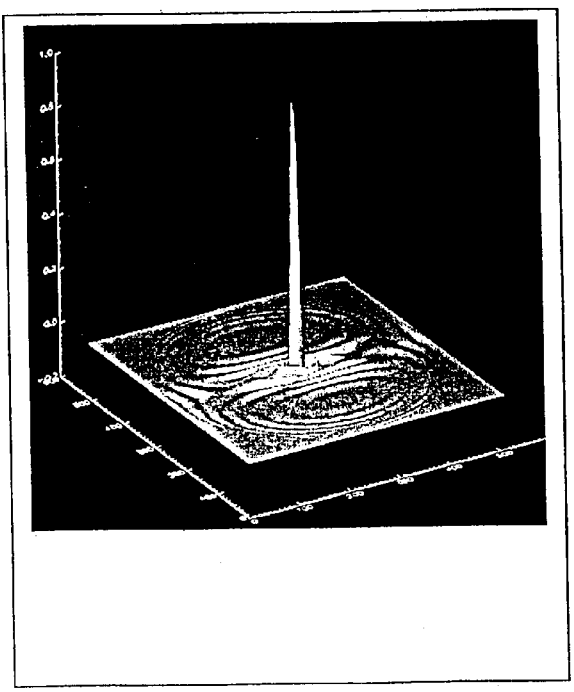
FIG. 4A shows the result of measuring the MTF of a human eye with an objective aberrometer.
Figure 4B:
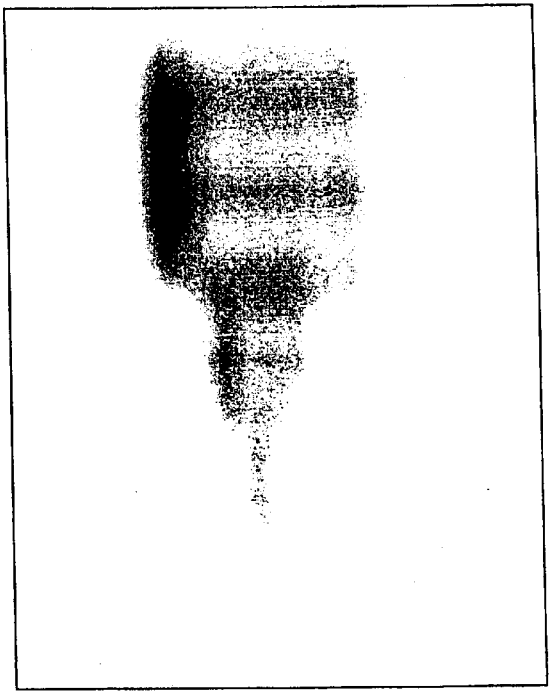
FIG. 4B shows a corresponding visual acuity chart computed according to a preferred embodiment of the invention.

FIGS. 4A–B show the results of measuring a human eye with an objective aberrometer, and applying the method described above to the computation of the visual acuity of a human subject. It is noted that the aberrations produce an MTF and visual acuity chart which are no longer symmetric, but which represent the effects of focus, astigmatism, and other higher order aberrations. The strong difference between horizontal and vertical visual acuity is seen in the MTF of FIG. 4A. The eye chart simulation of FIG. 4B, produced by convolution of the OTF whose MTF is shown in FIG. 4A, with the exemplary eye chart of FIG. 1B, indicates weak visual acuity in the horizontal direction, and reasonable acuity in the vertical. This agrees well with testimonial description from the subject regarding the subject's vision without the use of corrective lenses.

Subtraction of Specific Terms.

One key advantage to the numerical technique of computing the visual acuity image is that the effect of specific types of aberration may be considered. For example, it is quite common for a post-Lasik patient to complain of poor night vision, especially while driving. The patient may describe star shapes or double images surrounding headlights. In this case it may be desirable to isolate the effects of the various aberration terms in order to identify which is the most significant. This can be done by adjusting (e.g., adding to, subtracting from, eliminating, etc.) the appropriate terms in the aberration distribution that is used as the input to the algorithm.

This technique is particularly powerful when used with correction means that may introduce higher order aberrations in the process of correcting low order effects. As an example, it is common for the Lasik procedure to introduce significant spherical aberration in the process of correcting low order terms. Using the invention described herein, these effects could be correctly simulated to determine the effect on the subject's vision, before performing the procedure.

Figure 5:
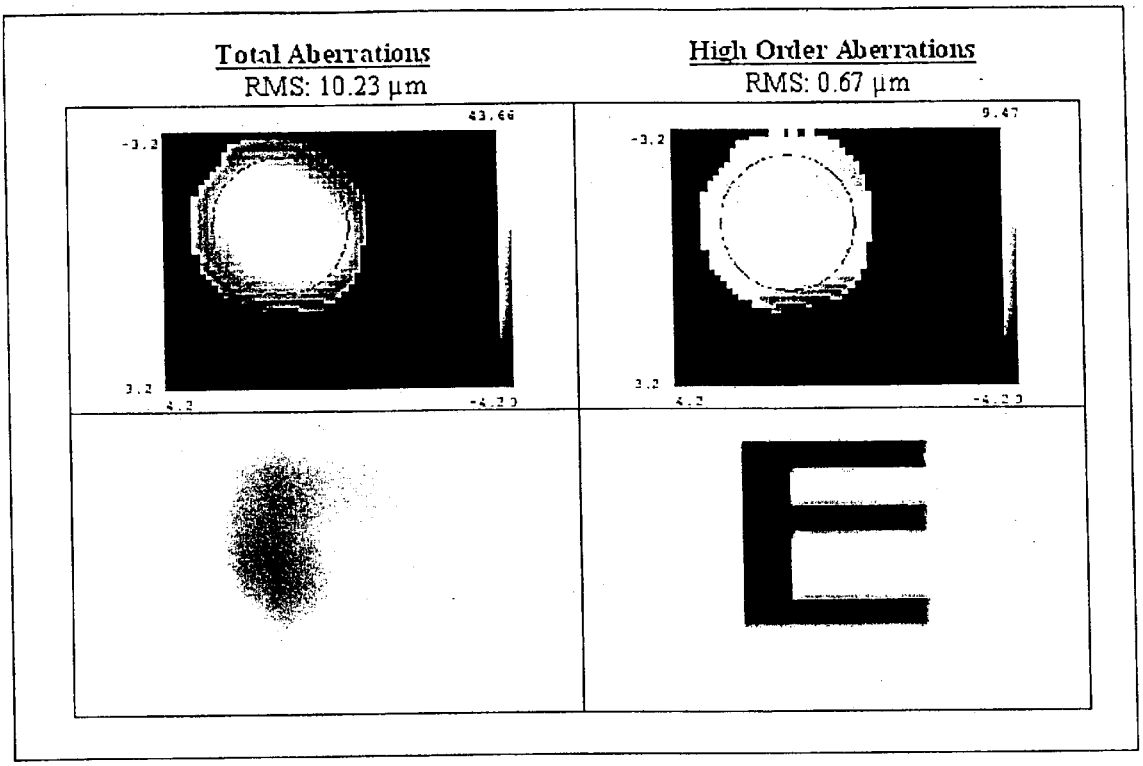
FIG. 5 illustrates the effect of subtracting the lower order Zernike terms (focus and astigmatism) from a wavefront before computation of a simulated image.

As an example of this, consider FIG. 5, which illustrates the effect of subtracting the lower order Zernike terms (focus and astigmatism) from the wavefront before computation of a simulated image. The left hand side of FIG. 5 shows the effect of all measured aberrations on a projected image, and right hand side of FIG. 5 shows the effect of only the higher order aberrations. This case is particularly useful since it represents correction of the ocular system with the best-fit conventional glasses. The residual aberrations can be evaluated for the effectiveness of other corrective means, or for screening and diagnosis.

Computation of the Visual Acuity Number.

One of the key parameters used to describe visual performance is the visual acuity number. This describes the comparative visual performance relative to a standard. Thus a subject is described as having 20/20, or 20/40 visual acuity. An objective means for determining this numerical representation is needed to allow interpretation of the measured aberration information. To determine the visual acuity number from the computed image, a special set of images may be used. The visual acuity is related to the ability to resolve a pair of points or targets. To this end a special set of images that may be test targets may be used to advantage. These may be sets of bars similar to an Air Force test target, or may be as simple as a pair of points with known separation. If the target image is configured with a number of different spatial frequencies, the resulting image (after convolution) may be used to automatically determine the visual acuity number.

Figure 6:
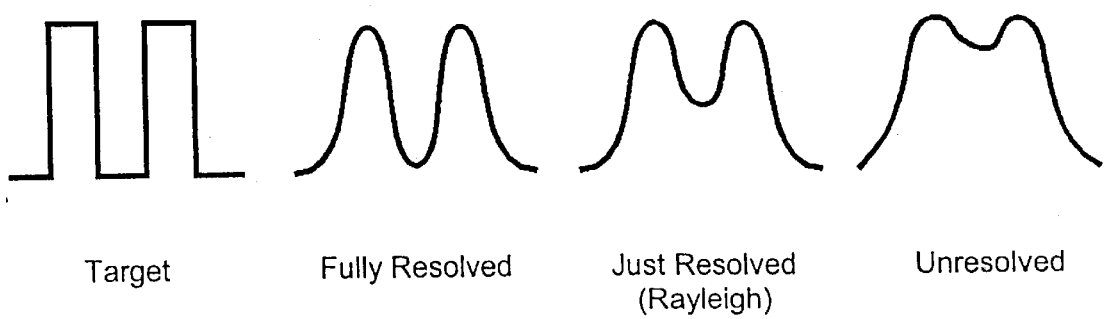
FIG. 6 presents a cross section through a target.
Figure 7:
FIG. 7 shows a simulated target that is used to determine a visual acuity number.

FIG. 7 shows a typical target that may be used to determine the visual acuity number. In this case a series of targets, each in different rows corresponding to a different visual acuity number (20/200, 20/50, 20/40, 20/20, etc.), is used as the input image to the convolution algorithm described herein. Each row contains targets with different spatial frequency information. By presenting several different targets for each line of a visual acuity number, the effect of non-symmetric aberrations may be included in the analysis. By determining the last line that may be distinguished, the visual acuity number may be measured. Each of these targets is analyzed using the Rayleigh or other criteria to determine if it meets the resolution requirements. The Rayleigh criteria states that two point or line sources may be considered distinguishable if the intensity distribution between the sources falls to ½ of the peak intensity, as shown in FIG. 6. FIG. 6 shows a cross section through a target. Proceeding from left to right, the first graph on the left shows a cross section through the original target, the second graph shows a resolved image of the target, the third graph shows the target image that just meets the Rayleigh criterion, and the last graph shows an unresolved image.

To determine the visual acuity number an image with a number of targets arranged in rows, each row consisting of the same size target corresponding to a given visual acuity. The targets may have both horizontal and vertical features, as appropriate. A section through each of the targets, in either the horizontal or vertical direction, as appropriate, is analyzed to determine if the Rayleigh criterion has been met for that target. If all targets on one row meet this criterion, but none on the next successive rows meet this criteria, then the visual acuity is the number associated with the last successful row.

Partial or fractional visual acuity may be obtained by counting the number of targets that pass the criteria on a given row. Other means for determining the visual acuity number from this arrangement of targets will be apparent to those skilled in the art.

A method for using measured wavefront information from an objective aberrometer to compute a simulated image has been presented. This method allows wavefront information to be interpreted in terms of a subject's visual performance, and allows a clinician to ascertain the effect of various aberrations. The visual acuity of the subject can be computed, either by a view of the computed eye chart, or through objective calculation of standardized targets. The effect on the subject visual performance of corrective means, including the effect of increased aberrations, can be computed, allowing evaluation of candidate treatments.

Several potential benefits may be obtained.

For example, conventional objective methods for measuring optical quality of the eye require a subjective evaluation by the interpreter. Accordingly, these conventional methods are not useful for measuring optical qualities for non-communicative subjects (e.g., deceased subjects, animals, infants, etc.). However, the methods described herein maybe used to predict the acuity of animal eyes both in vivo and ex vivo. Consequently, the usefulness of animal and cadaver studies of corrective measures can be increased.

Also, the methods described herein open the possibility of studying the relative importance of certain aberrations (such as spherical aberrations) for visual perception. Such a study may involve the combination of the objective measurements provided by the disclosed methods, in combination with subjective measurements (e.g., having a patient evaluate simulated acuity against what they perceive from an actual eye chart). This knowledge can lead to improvements in the manufacture of spectacles and contact lenses and improvement in surgical prescription techniques.

Moreover, according to the disclosed methods, it is possible for doctors to provide correction techniques by allowing them to show a prospective patient the potential improvement in their sight.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed is:

1. A method for computing the visual performance of a human or animal subject based on objective measurements of visual refraction including higher order aberrations, comprising the steps of:

measuring wavefront aberrations of a subject ocular pupil;

computing a point-spread-function from the measured pupil aberration;

providing a test image; and convolving the test image with the point-spread-function.

2. The method of claim 1 wherein the wavefront aberrations are measured with an objective aberrometer.

3. The method of claim 1 wherein the wavefront aberrations are measured with one selected from a group consisting of a Shack-Hartmann wavefront sensor system, a Tscherning aberrometer, a scanning resolved refractometer, and a Moire deflectometer.

4. The method of claim 1 where the wavefront aberrations are measured objectively by projecting a beam of light onto a retina and analyzing resulting return images.

5. The method of claim 1, further comprising producing a simulated image from a convolution result of convolving the test image with the point-spread-function.

6. The method of claim 1 wherein the test image is a Snellen acuity chart, and further comprising producing a simulated subject view of the Snellen acuity chart from a convolution result of convolving the Snellen acuity chart with the point-spread-function.

7. The method of claim 1 wherein convolving the test image with the point-spread-function comprises the steps of:

performing an inverse Fourier transform of a modulus squared of the point-spread-function to compute an optical transfer function;

computing a Fourier transform of the test image; and computing an inverse Fourier transform of a product of the optical transfer function and the test image Fourier transform.

8. The method of claim 7, wherein the Fourier transform and inverse Fourier transforms are computed with Fast Fourier Transforms.

9. A method for computing a point-spread-function of a human or animal ocular system from objective aberrometry measurements, comprising the steps of:

measuring a pupil aberration function with an objective aberrometer; arid computing the point-spread-function as a modulus squared of a Fourier transform of the measured pupil aberration function.

10. A method for determining a visual acuity of an ocular optical system, comprising:

measuring a pupil aberration function with an objective aberrometer;

computing a point-spread-function as a modulus squared of a Fourier transform of the measured pupil aberration function; and analyzing a spatial extent of the point-spread-function.

11. A method for determining Snellen acuity from evaluation of a double object when convolved with a point-spread-function, comprising the steps of:

measuring a subject pupil aberration function with an objective aberrometer;

computing a point-spread-function from the modified pupil aberration function;

computing an Optical Transfer Function (OTF) from the computed point-spread-function;

providing an input image which consists of appropriate targets coded so that known image features can be correlated to a visual acuity number; and convolving the input image with the point-spread-function by multiplying a Fourier transform of the input image by the OTF and then performing an inverse Fourier transform.

12. The method of claim 11 where the double object is a series of bars with different orientations.

13. A method for computing an image, comprising the steps of:

measuring wavefront aberrations of a subject ocular pupil;

computing a point-spread-function from the measured pupil aberration;

providing a test image;

convolving the test image with the point-spread-function; and producing a simulated image from a convolution result of convolving the test image with the point-spread-function, wherein at least one specific term of the point-spread-function is adjusted prior to the convolving step to simulate an effect of a correcting means.

14. The method of claim 13, wherein adjusting the specific term comprises subtracting the specific term from the point-spread-function.

15. A method for computing an effect of corrective means on a subject's visual acuity, comprising the steps of:

measuring a subject pupil aberration function with an objective aberrometer;

adjusting terms in the measured subject pupil aberration function that correspond to specific corrective means, producing a modified pupil aberration function;

computing a point-spread-function from the modified pupil aberration function;

computing an optical transfer function (OTF) of the computed point-spread-function;

multiplying a Fourier transform of a test image by the OTF to produce a Fourier result; and performing an inverse Fourier transform on the Fourier result.

16. The method of claim 15 wherein the corrective means is spectacle lenses.

17. The method of claim 15 wherein the corrective means is contact lenses.

18. The method of claim 15 wherein the corrective means is laser refractive surgery.

19. The method of claim 15 wherein the corrective means is Laser Thermal Keratotomy.

20. The method of claim 15, wherein the corrective means includes one selected from a group consisting of Interocular lenses, femto-second laser correction, and corneal implants.

21. A method of determining a best correction for a given subject, comprising the steps of:

measuring a subject pupil aberration function with an objective aberrometer;

subtracting terms from the pupil aberration function that correspond to specific corrective means, producing a modified pupil aberration function;

computing a point-spread-function from the modified pupil aberration function;

computing an optical transfer function (OTF) of the computed point-spread-function;

multiplying a Fourier transform of a test image by the OTF to produce a Fourier result;

performing an inverse Fourier transform on the Fourier result; and adjusting the terms that are subtracted to optimize a resultant image.

* * * * *